(12) United States Patent
Komori et al.

(10) Patent No.: US 11,600,401 B2
(45) Date of Patent: *Mar. 7, 2023

(54) BIOELECTRODE

(71) Applicant: NOK CORPORATION, Tokyo (JP)

(72) Inventors: Takayuki Komori, Fujisawa (JP); Ryo Futashima, Fujisawa (JP); Toru Uda, Fujisawa (JP); Yasushi Sugiyama, Fujisawa (JP)

(73) Assignee: NOK CORPORATION

( * ) Notice: Subject to any disclaimer, the term of this patent is extended or adjusted under 35 U.S.C. 154(b) by 206 days.

This patent is subject to a terminal disclaimer.

(21) Appl. No.: 16/877,529

(22) Filed: May 19, 2020

(65) Prior Publication Data

US 2020/0279669 A1 Sep. 3, 2020

Related U.S. Application Data

(63) Continuation of application No. PCT/JP2019/000910, filed on Jan. 15, 2019.

(30) Foreign Application Priority Data

Jan. 15, 2018 (JP) .............................. JP2018-004454

(51) Int. Cl.
| | | |
|---|---|---|
| *A61B 5/25* | (2021.01) | |
| *H01B 1/22* | (2006.01) | |
| *C08K 3/08* | (2006.01) | |
| *C08J 7/044* | (2020.01) | |
| *C08K 3/04* | (2006.01) | |
| *C09D 183/06* | (2006.01) | |
| *A61B 5/318* | (2021.01) | |
| *C08L 83/12* | (2006.01) | |

(52) U.S. Cl.
CPC ................ *H01B 1/22* (2013.01); *A61B 5/25* (2021.01); *A61B 5/318* (2021.01); *C08J 7/044* (2020.01); *C08K 3/04* (2013.01); *C08L 83/12* (2013.01); *C09D 183/06* (2013.01); *A61B 2562/0215* (2017.08); *C08J 2383/04* (2013.01); *C08K 3/08* (2013.01); *C08K 2003/0806* (2013.01); *C08K 2201/001* (2013.01)

(58) Field of Classification Search
None
See application file for complete search history.

(56) References Cited

U.S. PATENT DOCUMENTS

| | | | |
|---|---|---|---|
| 5,449,714 | A | 9/1995 | Inoue et al. |
| 6,010,646 | A | 1/2000 | Schleifstein |
| 10,184,779 | B2 | 1/2019 | Norisada et al. |
| 2008/0008757 | A1 | 1/2008 | Kessell et al. |
| 2012/0177934 | A1 | 7/2012 | Vogel et al. |
| 2017/0145257 | A1* | 5/2017 | Osada ..................... G06F 3/041 |
| 2018/0085019 | A1* | 3/2018 | Hatakeyama ............. C09J 11/04 |
| 2018/0116546 | A1 | 5/2018 | Pastoor et al. |
| 2020/0275850 | A1* | 9/2020 | Futashima ............... A61B 5/25 |
| 2020/0275853 | A1* | 9/2020 | Futashima ............. C08G 77/04 |
| 2020/0305746 | A1* | 10/2020 | Futashima ............... A61B 5/25 |

FOREIGN PATENT DOCUMENTS

| | | |
|---|---|---|
| CN | 1889928 A | 1/2007 |
| CN | 103237852 A | 8/2013 |
| CN | 104293222 A | 1/2015 |
| EP | 3 482 683 A1 | 5/2019 |
| JP | H06-166819 A | 6/1994 |
| JP | 2000-109631 A | 4/2000 |
| JP | 2003-125519 A | 4/2003 |
| JP | 2003-225217 A | 8/2003 |
| JP | 2005-131957 A | 5/2005 |
| JP | 2013-095822 A | 5/2013 |
| JP | 2014-221938 A | 11/2014 |
| JP | 2015-020329 A | 2/2015 |
| JP | 2015-041419 A | 3/2015 |
| JP | 2017128636 A | 7/2017 |
| WO | 2016/189422 A1 | 12/2016 |
| WO | 2018-008688 A1 | 1/2018 |

OTHER PUBLICATIONS

Decision of Refusal for related Japanese Patent Application No. 2019-564774 dated Oct. 18, 2021 with English translation (2 Pages).
Decision of Refusal for corresponding Japanese Application No. 2019-564772 dated Aug. 23, 2021, with English translation (4 pages).
Decision of Refusal for related Japanese Application No. 2019-564773 dated Aug. 23, 2021, with English translation (4 pages).
Extended European Search Report for corresponding Application No. 19738830.9 dated Aug. 13, 2021 (9 pages).
Cranny, A W J, et al., "Thick Film Silver-Silver Chloride Reference Electrodes", Measurement Science and Technology, IPO, Bristol, GB, vol. 9, No. 9, Sep. 1, 1998, pp. 1557-1565, XP020064598.
Extended European Search Report for related Application No. 19738971.1 dated Aug. 13, 2021 (9 pages).
International Search Report for corresponding International Application No. PCT/JP2019/000910 dated Apr. 16, 2019 (4 pages) with English translation.
International Search Report for corresponding International Application No. PCT/JP2019/000911 dated Apr. 16, 2019 (4 pages) with English translation.

(Continued)

*Primary Examiner* — David J Buttner

(74) *Attorney, Agent, or Firm* — Harness, Dickey & Pierce, P.L.C.

(57) ABSTRACT

A bioelectrode includes a conductive rubber electrode and a silver coating layer provided on the conductive rubber electrode and containing a silicone rubber and silver particles. The silver coating layer further contains a modified silicone.

3 Claims, 2 Drawing Sheets

(56) References Cited

OTHER PUBLICATIONS

International Search Report for corresponding International Application No. PCT/JP2019/000912 dated Apr. 16, 2019 (5 pages), with English translation.
International Preliminary Report on Patentability and Written Opinion for corresponding International Application No. PCT/JP2019/000910 dated Jul. 21, 2020 (11 pages) with English translation.
International Preliminary Report on Patentability and Written Opinion for corresponding International Application No. PCT/JP2019/000911 dated Jul. 21, 2020 (11 pages) with English Translation.
International Preliminary Report on Patentability and Written Opinion for corresponding International Application No. PCT/JP2019/000912 dated Jul. 21, 2020 (12 pages) with English translation.
Takeda, S., "The Latest Trend of Various Bioelectric Signal Measurement Electrodes", Special Edition, The Japanese Journal of Medical Instrumentation, vol. 80, No. 1 (2010) p. 28-p. 37 with English translation.
Japanese Office Action for corresponding Application No. JP 2019-564772 dated Mar. 22, 2021 with English translation (4 pages).
Japanese Office Action for related Application No. JP 2019-564773 dated Mar. 22, 2021 with English translation (5 pages).
Japanese Office Action for related Application No. JP 2019-564774 dated Apr. 19, 2021 with English translation (5 pages).
First Office Action dated Aug. 5, 2022 in the corresponding CN application No. 201980005849.9 w English Translation (12 pgs.).
First Office Action dated Aug. 10, 2022 in the relevant CN application No. 20198005789.0 with English Translation (12 pgs.).
U.S. Office Action for corresponding U.S. Appl. No. 16/877,534 dated Jun. 6, 2022 (30 Pages).
U.S. Office Action for corresponding U.S. Appl. No. 16/877,563 dated Jun. 3, 2022 (12 Pages).
Decision of Refusal issued in corresponding Chinese Application No. 2019800057890 dated Jan. 5, 2023, with English translation (8 Pages).

\* cited by examiner

BIOELECTRODE

CROSS REFERENCE TO RELATED APPLICATIONS

This is a continuation application of International Patent Application No. PCT/JP2019/000910 filed Jan. 15, 2019, which claims the benefit of Japanese Patent Application No. 2018-004454 filed Jan. 15, 2018, and the full contents of all of which are hereby incorporated by reference in their entirety.

BACKGROUND

Technical Field

The present disclosure relates to a bioelectrode.

Description of the Related Art

Bioelectrode materials made of metal such as sheets of highly conductive metals, for example, gold, silver, platinum, and copper have been conventionally used in bioelectrodes. These bioelectrode materials made of metal have poor adhesion to the skin, and detection of electrical signals from the skin is insufficient. When the materials are used as bioelectrodes, it is necessary to apply a gel, cream, paste, or the like to the skin. Additionally, metals, which are rigid, are not suitable to adhere for a long period.

There also exist bioelectrodes composed of an adhesive material such as a gel (also referred to as gel electrodes) (e.g., see The Japanese journal of medical instrumentation, Vol. 80, No. 1 (2010) P. 28-P. 37). In these bioelectrodes, application of a gel, cream, paste, or the like is not required, but trash and dust are likely to adhere to the adhesive material, and the adherence is gradually lost. For this reason, such bioelectrodes are not suitable for repetitive use. There are also known electrodes obtained by compounding carbon nanotubes in a rubber (e.g., see Japanese Patent Application Publication No. 2015-41419).

Electrodes in which carbon nanotubes and a conductive filler such as a metal powder of Cu, Ag, Au, Al, Ni, and the like are compounded exhibit electrical conductivity by direct contact among conductive filler constituents in the rubber. Such an electrode is formed by applying a coating liquid (paste) in which a conductive filler has been compounded to an uncured rubber on a substrate and then curing the rubber.

Meanwhile, the time from the application of the paste to the curing (hereinafter, also referred to as the standing time) may be set differently in accordance with production conditions, production modes, and the like in factories. For example, the paste may be cured immediately after the application or may be cured 30 minutes or 60 minutes after the application.

When a plurality of electrodes are produced, it is difficult to make the standing time of each electrode constant. For example, in the case where application of the paste is conducted on a plurality of electrodes part by part and sequentially and heating is conducted on the plurality of electrodes altogether, the standing time for electrodes on which the paste has been applied relatively early is long, and the standing time for electrodes on which the paste has been applied relatively late becomes shorter. The surface resistance of the electrodes after the curing varies or increases depending on the length of the standing time, and thus there may occur defective products of which surface resistance indicates an abnormal value.

SUMMARY

The present disclosure is related to providing a bioelectrode capable of lowering the occurrence ratio of defective products of which surface resistance indicates an abnormal value.

According to an aspect of the present disclosure, a bioelectrode includes a conductive rubber electrode and a silver coating layer provided on the conductive rubber electrode and containing a silicone rubber and silver particles. The silver coating layer further contains modified silicone.

In the aspect of the present disclosure, the silver coating layer preferably contains 1 part by mass or more of the modified silicone based on 100 parts by mass of a binder containing the silicone rubber.

In the aspect of the present disclosure, the silver coating layer preferably contains 2 parts by mass or more and 100 parts by mass or less of the modified silicone based on 100 parts by mass of a binder containing the silicone rubber.

In the aspect of the present disclosure, the modified silicone preferably includes at least one selected from the group consisting of polyether-modified silicones, polyether-alkyl-commodified silicones and polyglycerin-modified silicones, and polyglycerin-alkyl-commodified silicones.

According to the present disclosure, it is possible to provide a bioelectrode capable of lowering the occurrence ratio of defective products of which surface resistance indicates an abnormal value.

DETAILED DESCRIPTION

Hereinafter, embodiments of the present disclosure will be described with reference to the accompanying drawings. Note that the present disclosure is not limited by the following embodiments in any way.

Figure 1:
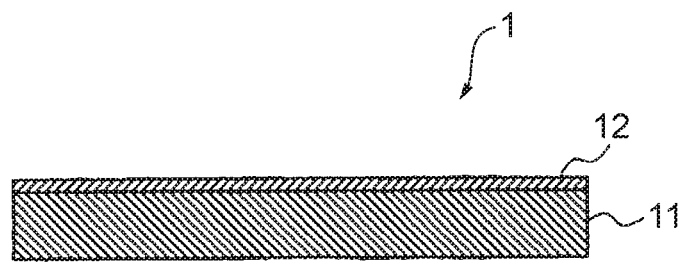
FIG. 1 is a cross-sectional view conceptually illustrating one example of a bioelectrode according to an embodiment of the present disclosure.

FIG. 1 is a cross-sectional view conceptually illustrating one example of a bioelectrode according to an embodiment of the present disclosure. As shown in FIG. 1, a bioelectrode 1 according to the present embodiment includes a conductive rubber electrode 11 and a silver coating layer 12 provided on the conductive rubber electrode 11.

The conductive rubber electrode 11 forms the main body of the bioelectrode 1, and the entire shape of the bioelectrode 1 is imparted by the shape of the conductive rubber electrode 11. The conductive rubber electrode 11 contains a rubber and conductive carbon particles.

As the rubber constituting the conductive rubber electrode 11, silicone rubbers and the like are exemplified. As the silicone rubber, it is possible to use various silicone rubbers in the range where the effects of the present disclosure are provided. Examples of the silicone rubber include organosilicon polymers and the like having a siloxane bond (—Si—O—) as the main chain and having a substituent such as a methyl group, a phenyl group, or a vinyl group and hydrogen as a side chain.

The conductive carbon particles are not limited as long as the particles can impart electrical conductivity to a rubber such as the silicone rubber mentioned above. Examples of the conductive carbon particles include carbon black and graphite. Examples of carbon black include Ketjen black and acetylene black. Among these, as the carbon black, Ketjen black and the like are preferable from the viewpoint of relatively high electrical conductivity.

There is no limitation on the average particle size of the conductive carbon particles. The average particle size of the conductive carbon particles is preferably in the range of 0.1 µm or more and 100 µm or less, more preferably in the range of 1 µm or more and 30 µm or less. In the present embodiment, the average particle size is an average diameter determined by measurement of an electron micrograph and calculation using the arithmetic mean.

There is no limitation on the amount of the conductive carbon particles to be compounded in the conductive rubber electrode 11. The amount to be compounded can be appropriately set in the range where electrical conductivity can be imparted, and is preferably in the range of 10% by mass or more and 70% by mass or less, more preferably in the range of 20% by mass or more and 50% by mass or less.

The silver coating layer 12 is obtained by compounding silver particles to a silicone rubber. The silicone rubber is not especially limited, but ones having a siloxane bond (—Si—O—) as the main chain are preferable, and ones having an organosilicon polymer or the like having a substituent such as a methyl group, a phenyl group, or a vinyl group and hydrogen as a side chain are preferable.

When the silver coating layer 12 is constituted with a silicone rubber, the silicone rubber serves as a binder for the silver particles. Especially, the silver coating layer 12 is retained on the conductive rubber electrode 11 formed of the silicone rubber with a high adhesion, and thus it is possible to prevent the layer from coming off from the electrode. This adhesion also contributes to stabilization of electrical connection between the silver coating layer 12 and the conductive rubber electrode 11. Additionally, a silicone rubber has excellent flexibility, and thus, conformability to movements of a living body is suitably exhibited during use of the bioelectrode 1. As a result of these, it is possible to suitably reduce the contact impedance with a living body.

In the present embodiment, the silver coating layer 12 further contains a modified silicone. The silver particles form a network of the conductive particles (silver particles) in the silver coating layer 12 to thereby impart electrical conductivity to the silver coating layer 12 constituting the bioelectrode. Meanwhile, an effect of enabling the occurrence ratio of defective products of which surface resistance indicates an abnormal value to be lowered is exhibited by causing the silver coating layer 12 to further contain a modified silicone.

That is, on producing the bioelectrode 1, even if the length of the standing time from the application of the silver paste to the curing for forming the silver coating layer 12 varies, a variation or increase in the surface resistance of the bioelectrode after the curing is suppressed by compounding the modified silicone in advance.

As the modified silicone, ones obtained by introducing a side chain that causes modification to the main chain formed of a siloxane bond (—Si—O—; also referred to as a silicone chain) can be preferably used. Examples thereof include silicones containing polyether modification, polyether-alkyl commodification, polyglycerin modification, polyglycerin-alkyl commodification, or the like. The side chain that causes modification preferably contains an ether bond (—C—O—C—).

As the polyether-modified silicone, ones obtained by introducing a side chain formed of polyether into the main chain formed of a silicone chain can be used.

As the polyether-alkyl-commodified silicone, ones obtained by introducing a side chain formed of a polyether chain and a side chain formed of an alkyl chain to the main chain formed of a silicone chain can be used.

As the polyglycerin-modified silicone, ones obtained by introducing a side chain formed of a polyglycerin chain into the main chain formed of a silicone chain can be used.

As the polyglycerin-alkyl-commodified silicone, ones obtained by introducing a side chain formed of a polyglycerin chain and a side chain formed of an alkyl chain into the main chain formed of a silicone chain can be used. Among these, the polyether-modified silicone or polyglycerin-modified silicone is particularly preferable.

The modified silicone preferably has a viscosity of 100 $mm^2/s$ or more and 5000 $mm^2/s$ or less and an HLB of about 1 or more and 15 or less. One of the modified silicones may be used singly or a plurality of the modified silicones may be used in combination.

The amount of the modified silicone to be added in the silver coating layer 12 is preferably 1 part by mass or more, further preferably 2 parts by mass or more based on 100 parts by mass of a binder formed of a silicone rubber, in the viewpoint of further satisfactorily exhibiting the effects of the present disclosure. The upper limit of the amount of the modified silicone to be added is not especially limited, can be appropriately set in the range where the silicone rubber can be cured, and can be set to 100 parts by mass or less, for example.

The silver particles are not especially limited as long as the silver particles are dispersible in the silicone rubber. For example, at least one type of aggregated silver powders and flaky silver powders can be used. An aggregated silver powder and a flaky silver powder may be mixed and used, or either one type of them may be used.

The aggregated silver powder refers to a silver powder of a plurality of particulate primary particles three-dimensionally aggregated, and an example thereof can be trade name: "G-35" (manufactured by DOWA Electronics Materials Co., Ltd.).

The flaky silver powder refers to a silver powder having a scale-like shape, and examples thereof can include trade name: "327077" (manufactured by Sigma-Aldrich Co. LLC.) and trade name: "FA-D-3" (manufactured by DOWA Electronics Materials Co., Ltd.).

The average particle size of the silver particles is not especially limited, but is preferably in the range of 4 µm or more and 8 µm or less in the case of aggregated ones and preferably in the range of 5 µm or more and 15 µm or less in the case of flaky ones. The average particle size is an average diameter determined by measurement of an electron micrograph and calculation using arithmetic mean.

The total amount of the silver particles to be compounded in the silver coating layer 12 can be appropriately set in the range where electrical conductivity can be imparted, but is preferably in the range of 50 parts by mass or more and 600 parts by mass or less, more preferably in the range of 100 parts by mass or more and 400 parts by mass or less, based on 100 parts by mass of the silicone rubber.

The film thickness of the silver coating layer 12 is not especially limited and is preferably in the range of 10 µm or more and 300 μm or less, more preferably in the range of 15 μm or more and 100 μm or less. This can further enhance adhesion of the silver coating layer 12 with respect to the conductive rubber electrode 1, further prevent delamination of the silver coating layer 12, and additionally lower the contact impedance.

Figure 2:
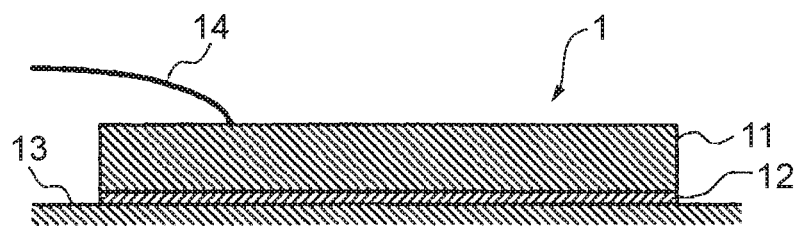
FIG. 2 is a view conceptually illustrating a usage example of the bioelectrode according to the embodiment of the present disclosure.

In the case of the conductive rubber electrode 11 mentioned above is in the form of sheet, the film thickness of the silver coating layer 12 can be made smaller than the film thickness of the conductive rubber electrode 11. For example, as shown in FIG. 2, by use of the bioelectrode 1 according to the present embodiment, the conductive rubber electrode 11 is connected to a measuring apparatus via a signal transmission member 14 such as wiring, the surface of the silver coating layer 12 is caused to contact a living body 13, and electrical signals from the living body 13 can be measured in the measuring apparatus.

The bioelectrode 1 according to the present embodiment can be suitably used for measuring an electrocardiogram as electrical signals. The bioelectrode 1 according to the present embodiment also can be suitably used in medical measuring apparatuses, wearable measuring apparatuses, and health monitoring devices, for example.

One example of a method for producing the bioelectrode 1 according to the present embodiment will be described hereinafter. First, a conductive rubber electrode 11 is provided, and a silver coating layer 12 is formed on the conductive rubber electrode 11. On forming the silver coating layer 12, first, silver particles and a modified silicone are mixed to an uncured liquid silicone rubber (binder), and the mixture is stirred to prepare a silver paste. Meanwhile, it is possible to appropriately compound a crosslinking agent for crosslinking (curing) the silicone rubber to the silver paste. Thereafter, the silver paste prepared is applied on the conductive rubber electrode 11. Curing the silver paste applied by heating causes the silver coating layer 12 to be formed.

Meanwhile, even if the length of the standing time from the application of the silver paste to the curing for forming the silver coating layer 12 varies, a variation or increase in the surface resistance of the bioelectrode 1 after the curing is suppressed by using the modified silicone. For this reason, it is possible to lower the occurrence ratio of defective products of which surface resistance indicates an abnormal value and to improve the yield of bioelectrodes satisfying the conditions of a predetermined surface resistance value.

Furthermore, the bioelectrode 1 according to the present embodiment has excellent flexibility, which is derived from a silicone rubber or modified silicone. Thus, even when fitted for a long period, the bioelectrode 1 causes no discomfort and can suitably conform to movements of a living body.

The shape of the bioelectrode according to the present embodiment is not limited to a sheet shape and can be formed into various shapes. Meanwhile, the electrode surface part to be contacted with a living body can be constituted by the silver coating layer 12 mentioned above.

EXAMPLES

Hereinafter, the present disclosure will be described more in detail based on examples conducted to clarify the effects of the present disclosure. Note that the present disclosure is not limited by the following examples and comparative examples in any way.

1. Production of Bioelectrode

Example 1

(1) Production of Conductive Rubber Electrode

To 100 parts by mass of a conductive silicone rubber ("KE-3801M-U" manufactured by Shin-Etsu Chemical Co., Ltd.; containing carbon black), 1.0 part by mass of a crosslinking agent ("C-8A" manufactured by Shin-Etsu Chemical Co., Ltd.; 2,5-dimethyl-2,5-bis(t-butylperoxy)hexane content: 80% by mass) was compounded.

Thereafter, a material obtained by kneading the components compounded described above in a kneader for 10 minutes and then further kneading the components with a roll for three minutes, (carbon black content: 6% by volume) was press-crosslinked (primary-crosslinked) at 180° C. for four minutes and thereafter secondary-crosslinked at 230° C. for five hours to provide a conductive rubber electrode having a thickness of 1 mm.

(2) Formation of Silver Coating Layer

To 100 parts by mass of a liquid silicone rubber ("KE-106" manufactured by Shin-Etsu Chemical Co., Ltd.) as a binder, 150 parts by mass of each of two types of silver particles ("G-35" and "FA-D-3"; both manufactured by DOWA Electronics Materials Co., Ltd.) (total amount to be compounded: 300 parts by mass) and additionally 0.5 parts by mass of a polyglycerin-modified silicone ("KF-6100" manufactured by Shin-Etsu Chemical Co., Ltd.) as a modified silicone were mixed, and the mixture was stirred to prepare a silver paste.

Thereafter, the silver paste prepared was applied homogeneously on the conductive rubber electrode obtained in the above-described "(1) Production of Conductive Rubber Electrode".

In order to compare variations in the resistance value of the bioelectrode, the silver paste was applied and left for 0 minutes, 30 minutes, and 60 minutes. Then, the paste was cured for 30 minutes in an oven set at 150° C. to form a silver coating layer so as to have a thickness of 50 μm.

The rubber electrode produced as mentioned above (sheet form) was punched to a size having a diameter of 19 mm to produce a bioelectrode.

Example 2

A bioelectrode was produced in the same manner as in Example 1 except that the amount of the modified silicone added was changed to 1 part by mass.

Example 3

A bioelectrode was produced in the same manner as in Example 1 except that the amount of the modified silicone added was changed to 2 parts by mass.

Example 4

A bioelectrode was produced in the same manner as in Example 1 except that the amount of the modified silicone added was changed to 3 parts by mass.

Example 5

A bioelectrode was produced in the same manner as in Example 1 except that the amount of the modified silicone added was changed to 30 parts by mass.

Example 6

A bioelectrode was produced in the same manner as in Example 1 except that the amount of the modified silicone added was changed to 100 parts by mass.

Example 7

A bioelectrode was produced in the same manner as in Example 1 except that 10 parts by mass of a polyglycerin-modified silicone (trade name: "KF-6106", manufactured by Shin-Etsu Chemical Co., Ltd.) was used as the modified silicone.

Example 8

A bioelectrode was produced in the same manner as in Example 4 except that a polyether-modified silicone (trade name: "KF-6015", manufactured by Shin-Etsu Chemical Co., Ltd.) was used as the modified silicone.

Example 9

A bioelectrode was produced in the same manner as in Example 8 except that the amount of the modified silicone added was changed to 10 parts by mass.

Example 10

A bioelectrode was produced in the same manner as in Example 9 except that a polyether-modified silicone (trade name: "KF-6011", manufactured by Shin-Etsu Chemical Co., Ltd.) was used as the modified silicone.

Example 11

A bioelectrode was produced in the same manner as in Example 1 except that 5 parts by mass of a polyglycerin-modified silicone (trade name: "KF-6106", manufactured by Shin-Etsu Chemical Co., Ltd.) and 5 parts by mass of a polyether-modified silicone (trade name: "KF-6015", manufactured by Shin-Etsu Chemical Co., Ltd.) were used in combination as the modified silicone.

Example 12

A bioelectrode was produced in the same manner as in Example 11 except that 10 parts by mass of a polyglycerin-modified silicone (trade name: "KF-6106", manufactured by Shin-Etsu Chemical Co., Ltd.) and 10 parts by mass of a polyether-modified silicone (trade name: "KF-6015", manufactured by Shin-Etsu Chemical Co., Ltd.) were used in combination as the modified silicone.

Comparative Example 1

A bioelectrode was produced in the same manner as in Example 1 except that compounding of the modified silicone was omitted.

2. Method for Measuring Electrical Characteristics

In each of Examples and Comparative Example, each electrode of which the time from the application of the silver paste to curing (hereinafter, also referred to as the standing time) was changed to the time described in Table 1 was measured for the surface resistance. Additionally, the change rate in the surface resistance value due to the standing time was calculated. The results are shown in Table 1.

TABLE 1

|  | Modified silicone | | Surface resistance value [Ω] | | Change rate (times) | |
| --- | --- | --- | --- | --- | --- | --- |
|  | Type | Amount added*1 | After 0 minutes | After 60 minutes | 0 minutes to 60 minutes | 30 minutes to 60 minutes |
| Example 1 | K F-6100 (Polyglycerin-modified silicone) | 0.5 | 0.6 | 3 | 5.00 | 0.50 |
| Example 2 | KF-6100 | 1 | 0.3 | 0.4 | 1.33 | 0.27 |
| Example 3 | KF-6100 | 2 | 0.11 | 0.6 | 5.45 | 1.50 |
| Example 4 | KF-6100 | 3 | 0.18 | 0.2 | 1.11 | 0.50 |
| Example 5 | KF-6100 | 30 | 0.09 | 0.12 | 1.33 | 1.33 |
| Example 6 | KF-6100 | 100 | 0.09 | 0.12 | 1.33 | 1.20 |
| Example 7 | KF-6106 (Polyglycerin-modified silicone) | 10 | 0.07 | 0.13 | 1.86 | 2.17 |
| Example 8 | KF-6015 (Polyether-modified silicone) | 3 | 0.06 | 0.2 | 3.33 | 2.50 |
| Example 9 | KF-6015 | 10 | 0.05 | 0.07 | 1.40 | 0.54 |
| Example 10 | KF-6011 (Polyether-modified silicone) | 10 | 0.16 | 0.05 | 0.31 | 0.63 |
| Example 11 | KF-6106 KF-6015 mixture of 2 types | Each 5, 10 in total | 0.03 | 0.15 | 5.00 | 5.00 |
| Example 12 | KF-6106 KF-6015 mixture of 2 types | Each 10, 20 in total | 0.05 | 0.09 | 1.80 | 1.50 |
| Comparative Example 1 | No | No | 0.19 | 6 | 31.58 | 9.68 |

*1: The amount of the dispersant added is expressed in parts by mass based on 100 parts by mass of the binder.

3. Evaluation of Electrical Characteristics

In Examples 1 to 12, in which the silver coating layer was caused to contain the modified silicone, it can been seen that a variation or increase in the surface resistance of the bioelectrode after the curing is suppressed, irrespective of the length of the standing time from the application of the silver paste to the curing. Thus, it is possible to lower the occurrence ratio of defective products of which surface resistance indicates an abnormal value.

In contrast, in Comparative Example 1, in which compounding of the modified silicone was omitted, it can be seen that the surface resistance increases markedly when the standing time becomes longer. For this reason, the occurrence ratio of defective products of which surface resistance indicates an abnormal value increases.

4. Method for Evaluating Strain Resistance

Figure 3:
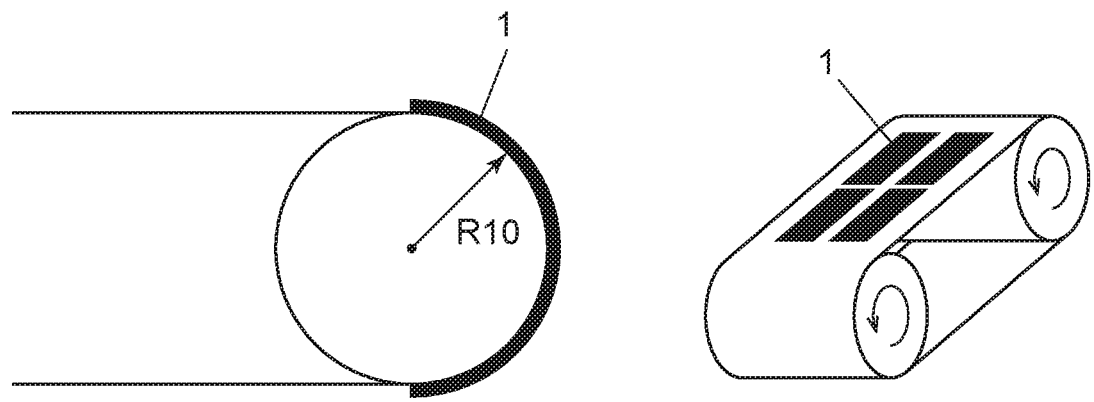
FIG. 3 is a conceptual view of a conveyor belt used in a bending test.
Figure 4:
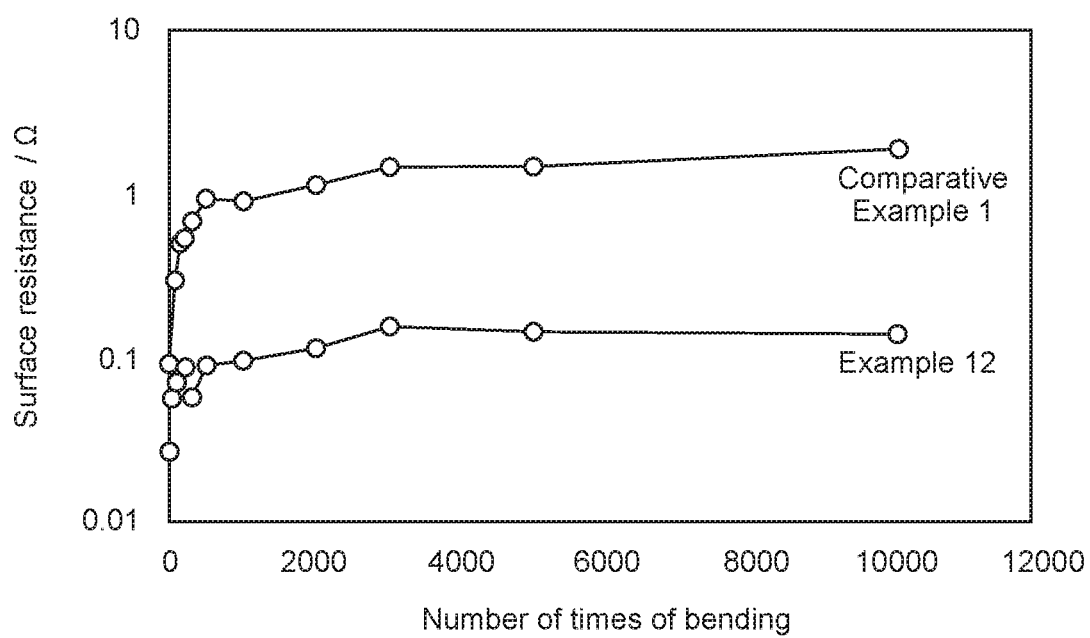
FIG. 4 is a view illustrating dependency of the surface resistance on the number of times of bending.

Bioelectrodes produced with the same compounding formulation as in Example 12 and Comparative Example 1 were punched into a size of 20 mm×60 mm. A bending test was conducted in which the surface of the conductive rubber electrode of each bioelectrode was attached onto a conveyor belt illustrated in FIG. 3 and rotated to repetitively apply deformation (external force). Here, each bioelectrode was bent at a radius of 10 mm, and a total of 10000 times of bending was conducted in 5000 seconds (2 times/second). The surface resistance of the silver coating layer surface was measured every prescribed number of times by a four-terminal method using a low resistivity meter "Loresta" manufactured by Mitsubishi Chemical Analytech Co., Ltd. (using a PSP terminal). The results are shown in FIG. 4. Additionally, the measurement results of the change rate of the surface resistance after 10000 times of bending with respect to the initial surface resistance are shown in Table 2.

TABLE 2

| | Bending test (strain resistance) | | |
| --- | --- | --- | --- |
| | Initial surface resistance [Ω] | Surface resistance after 10000 times of bending [Ω] | Change rate [times] |
| Example 12 | 0.0269 | 0.146 | 5.43 |
| Comparative Example 1 | 0.0916 | 2.03 | 22.2 |

5. Evaluation of Strain Resistance

As shown in Table 2 and FIG. 4, when the bending test was conducted 10000 times, the absolute value of the surface resistance of the bioelectrode of Example 12 was one-tenth or less of that of Comparative Example 1. The change ratio of the surface resistance was 22 times in Comparative Example 1, whereas that in Example 12 stayed at 5.4 times. From the above, it can be seen that a property with which satisfactory electrical conductivity can be maintained even under repetitive deformation (strain resistance) is improved by causing the silver coating layer 12 to contain the modified silicone. From this result, it can also be seen that a conductive network to be formed with the silver particles is more unlikely to be cut even under repetitive deformation by causing the silver coating layer to contain the modified silicone.

What is claimed is:

1. A bioelectrode comprising:

a conductive rubber electrode; and a silver coating layer provided on the conductive rubber electrode and containing a silicone rubber and silver particles, wherein the silver coating layer further contains a modified silicone, and the modified silicone includes at least one selected from the group consisting of polyglycerin-method silicones and polyglycerin-alkyl-commodified silicones.

2. The bioelectrode according to claim 1, wherein the silver coating layer contains 1 part by mass or more of the modified silicone based on 100 parts by mass of a binder containing the silicone rubber.

3. The bioelectrode according to claim 2, wherein the silver coating layer contains 2 parts by mass or more and 100 parts by mass or less of the modified silicone based on 100 parts by mass of a binder containing the silicone rubber.

* * * * *